United States Patent
Sakai

(10) Patent No.: US 10,420,599 B2
(45) Date of Patent: Sep. 24, 2019

(54) ULTRASONIC VIBRATOR AND ULTRASONIC TREATMENT DEVICE

(71) Applicant: OLYMPUS CORPORATION, Tokyo (JP)

(72) Inventor: Nagahide Sakai, Tokyo (JP)

(73) Assignee: Olympus Corporation, Tokyo (JP)

( * ) Notice: Subject to any disclaimer, the term of this patent is extended or adjusted under 35 U.S.C. 154(b) by 244 days.

(21) Appl. No.: 15/427,692

(22) Filed: Feb. 8, 2017

(65) Prior Publication Data

US 2017/0143399 A1 May 25, 2017

Related U.S. Application Data

(63) Continuation of application No. PCT/JP2014/075101, filed on Sep. 22, 2014.

(51) Int. Cl.
| | |
|---|---|
| H01L 41/09 | (2006.01) |
| A61B 18/00 | (2006.01) |
| H01L 41/253 | (2013.01) |
| B06B 1/06 | (2006.01) |
| H01L 41/047 | (2006.01) |
| H01L 41/187 | (2006.01) |
| H02N 2/06 | (2006.01) |
| A61B 17/32 | (2006.01) |
| H01L 41/083 | (2006.01) |

(52) U.S. Cl.
CPC ...... *A61B 18/00* (2013.01); *A61B 17/320068* (2013.01); *A61B 17/320092* (2013.01); *B06B 1/0607* (2013.01); *B06B 1/0611* (2013.01); *H01L 41/047* (2013.01); *H01L 41/083* (2013.01); *H01L 41/09* (2013.01); *H01L 41/1873* (2013.01); *H01L 41/253* (2013.01); *H02N 2/06* (2013.01)

(58) Field of Classification Search
CPC ...... H02N 2/06; H01L 41/1873; H01L 41/083
USPC ......................................................... 310/328
See application file for complete search history.

(56) References Cited

U.S. PATENT DOCUMENTS

| | | | |
|---|---|---|---|
| 7,671,518 B2 | 3/2010 | Sawada et al. | |
| 2002/0185936 A1* | 12/2002 | Barber | G04F 5/063 310/328 |
| 2006/0175929 A1 | 8/2006 | Sawada et al. | |

FOREIGN PATENT DOCUMENTS

| | | |
|---|---|---|
| CN | 101238754 A | 8/2008 |
| DE | 10 2004 011 377 A1 | 9/2005 |
| JP | 2002-128259 A | 5/2002 |

(Continued)

OTHER PUBLICATIONS

International Search Report dated Dec. 16, 2014 issued in PCT/JP2014/075101.

*Primary Examiner* — Jaydi San Martin
(74) *Attorney, Agent, or Firm* — Scully Scott Murphy & Presser, P.C.

(57) ABSTRACT

An ultrasonic vibrator and an ultrasonic treatment device which can adjust a resonant frequency while maintaining driving force are provided. An ultrasonic vibrator 1 includes two metal blocks 2, a driving unit 3 that is arranged between the metal blocks 2 and produces a piezoelectric effect to vibrate by application of an alternating voltage, and at least one adjustment unit 4 that is arranged between the metal blocks 2 and the driving unit 3 in an insulated state and changes Young's modulus.

9 Claims, 20 Drawing Sheets

(56) References Cited

FOREIGN PATENT DOCUMENTS

| JP | 2006-254683 A | 9/2006 |
| JP | 2014-144147 A | 8/2014 |

* cited by examiner

ULTRASONIC VIBRATOR AND ULTRASONIC TREATMENT DEVICE

CROSS-REFERENCE TO RELATED APPLICATIONS

This application is based on PCT/JP2014/075101 filed on Sep. 22, 2014. The contents of the PCT application is incorporated herein by reference.

BACKGROUND OF THE INVENTION AND RELATED ART STATEMENT

The present invention relates to an ultrasonic vibrator and an ultrasonic treatment device which excite ultrasonic waves.

Piezoelectric elements that use a piezoelectric effect for driving have been conventionally used in various applications such as an ultrasonic vibrator. The resonant frequency of such a piezoelectric element changes with slight variations in dimension etc. Adjustments need to be made to obtain a desired value.

For example, a technique has been disclosed in which driving electrodes to which a voltage is applied are arranged over an entire plane lying in a driving direction of a piezoelectric element, and some adjustment electrodes among the driving electrodes are electrically disconnected to adjust the resonant frequency (see JP 2006-254683 A).

SUMMARY OF INVENTION

An ultrasonic vibrator according to an aspect of the present invention includes: two metal blocks; a driving unit that is arranged between the metal blocks and produces a piezoelectric effect to vibrate by application of an alternating voltage; and at least one adjustment unit that is arranged between the metal blocks and the driving unit in an insulated state and changes Young's modulus.

An ultrasonic treatment device according to an aspect of the present invention includes the foregoing ultrasonic vibrator, and an end portion to which ultrasonic vibrations generated by the ultrasonic vibrator are transmitted and which treats living body tissue.

DESCRIPTION OF EMBODIMENTS

An ultrasonic vibrator 1 according to the present embodiment will be described below.

Figure 1:
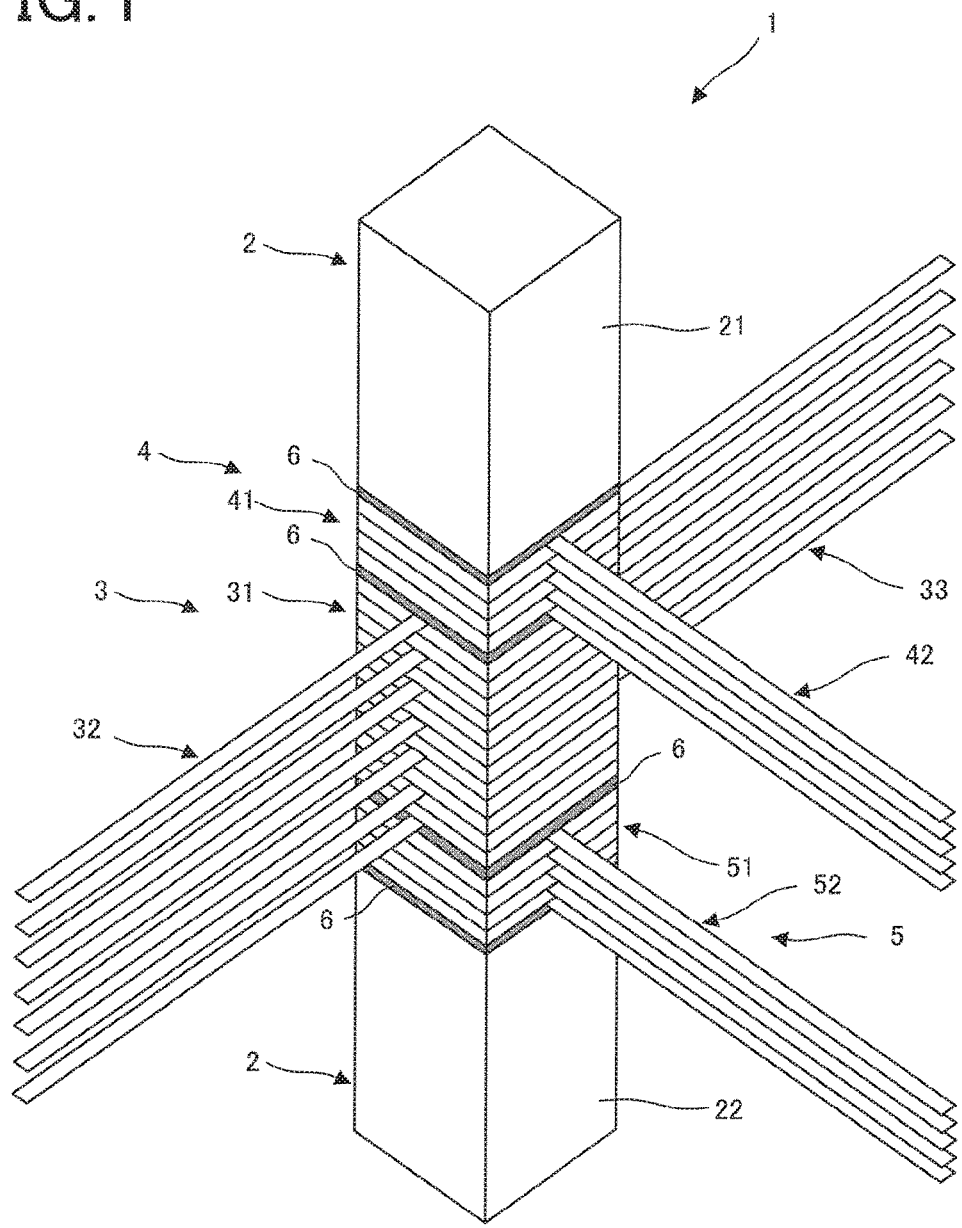
FIG. 1 illustrates a perspective view of an ultrasonic vibrator according to the present embodiment.

FIG. 1 illustrates a perspective view of the ultrasonic vibrator 1 according to the present embodiment.

As illustrated in FIG. 1, the ultrasonic vibrator 1 according to the present embodiment includes metal blocks 2 including a first metal block 21 and a second metal block 22, a driving piezoelectric element unit 3 including a plurality of driving piezoelectric elements 31 stacked between the first metal block 21 and the second metal block 22, a first adjustment piezoelectric element unit 4 including a plurality of first adjustment piezoelectric elements 41 stacked between the first metal block 21 and the driving piezoelectric element 3, and a second adjustment piezoelectric element unit 5 including a plurality of second adjustment piezoelectric elements 51 stacked between the second meatal block 22 and the driving piezoelectric element unit 3.

Here, the driving piezoelectric element unit 3 constitutes a driving unit. The first adjustment piezoelectric element unit 4 and the second adjustment piezoelectric element unit 5 constitute an adjustment unit.

The first metal block 21 and the first adjustment piezoelectric element unit 4, the first adjustment piezoelectric element unit 4 and the driving piezoelectric element unit 3, the driving piezoelectric element unit 3 and the second adjustment piezoelectric element unit 5, and the second adjustment piezoelectric element unit 5 and the second metal block 22 are closely contacted and bonded to each other by a bonding material 6. The driving piezoelectric elements 31, the first adjustment piezoelectric elements 41, and the second adjustment piezoelectric elements 51 are also closely contacted and bonded to each other by a not-illustrated bonding material.

In the ultrasonic vibrator 1 according to the present embodiment, the metal blocks 2, the driving piezoelectric elements 31, the first adjustment piezoelectric elements 41, and the second adjustment piezoelectric elements 51 have a rectangular cross section for bonding. Electrodes 32, 33, 42, and 52 are attached to the piezoelectric elements. Driving electrodes 32 and 33 of the driving piezoelectric element unit 3 are each connected to every other one of the driving piezoelectric elements 31 which are stacked to alternate in the direction of polarization. For example, the first driving electrodes 32 are attached to odd-numbered driving piezoelectric elements 31 from the first adjustment piezoelectric element unit 4 side. The second driving electrodes 33 are attached to even-numbered driving piezoelectric elements 31 from the first adjustment piezoelectric element unit 4 side. The first driving electrodes 32 and the second driving electrodes 33 are connected to two separate electrodes of an alternating-current power supply to be described later, respectively.

Now, materials of the ultrasonic vibrator 1 according to the present embodiment will be described.

The metal block 2 is made of an aluminum alloy such as duralumin, a titanium alloy, pure titanium, stainless steel, soft steel, nickel chrome steel, tool steel, brass, a Monel metal, or the like.

The driving piezoelectric elements 31, the first adjustment piezoelectric elements 41, and the second adjustment piezoelectric elements 51 are preferably made of a lithium niobate single crystal which has a high Curie point. For example, a lithium niobate wafer having a crystal orientation called 36°-rotated Y-cut is preferably used to increase the electromechanical coupling coefficients of the piezoelectric elements 31, 41, and 51 in a thickness direction. Underlayer metal films of Ti/Pt, Cr/Ni/Au, or the like are deposited on the surface and backside of the lithium niobate wafer to improve wettability and adhesiveness between lithium niobate and lead-free solder. The resultant is then cut into rectangular piezoelectric elements by dicing etc.

Lead-free solder having a melting point lower than the Curie point, preferably a melting point lower than or equal to one half the Curie point, is used as the bonding material 6. If solder is used as the bonding material and the solder is supplied in the form of solder pellets, parts having uneven shapes are difficult to bond without bubbles. The surfaces of the metal blocks 2 and the piezoelectric elements 31, 41, and 51 to which the bonding material is applied are therefore preferably configured as flat surfaces.

Figure 2:
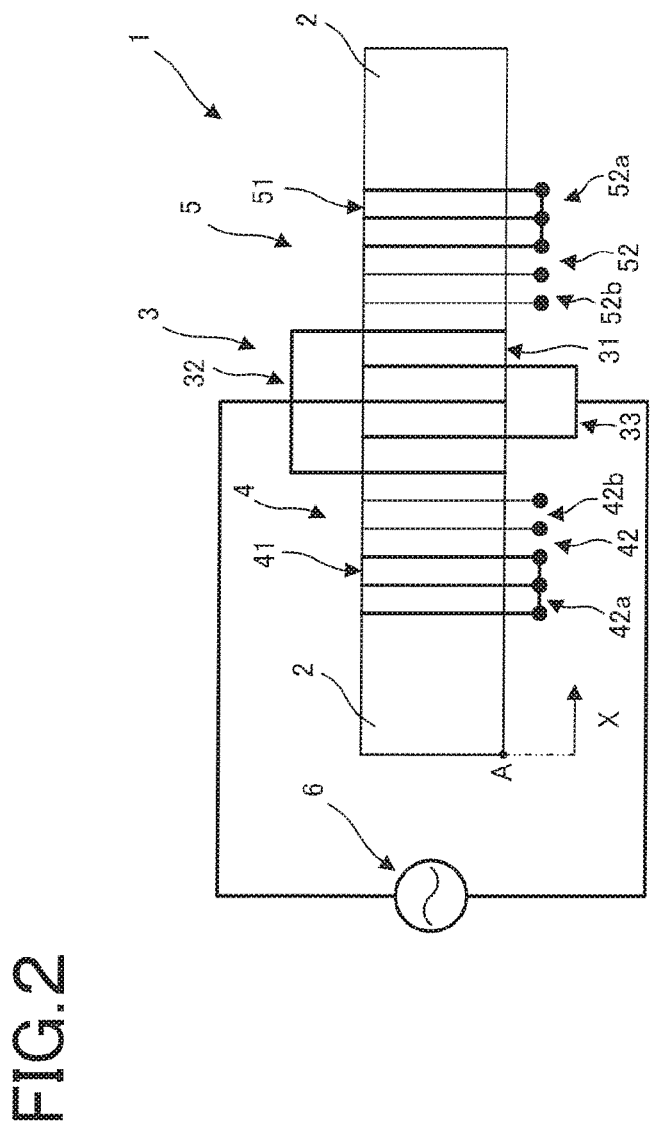
FIG. 2 illustrates a schematic diagram of the ultrasonic vibrator with design values of the present embodiment.
Figure 3:
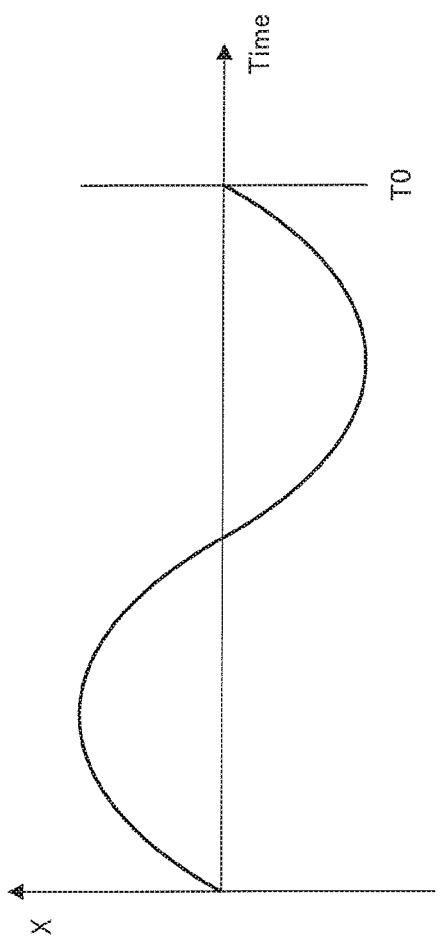
FIG. 3 illustrates one period of the ultrasonic vibrator with the design values of the present embodiment.

FIG. 2 illustrates a schematic diagram of the ultrasonic vibrator 1 with design values of the present embodiment. FIG. 3 illustrates one period of the ultrasonic vibrator 1 with the design values of the present embodiment.

As illustrated in FIG. 2, in the ultrasonic vibrator 1 with the design values of the present embodiment, the first driving electrodes 32 of the driving piezoelectric element unit 3 are connected to one electrode of an alternating-current power supply 6. The second driving electrodes 33 are connected to the other electrode of the alternating-current power supply 6. Among first adjustment electrodes 42, a predetermined number of electrodes are short-circuited as first initial short circuit electrodes 42a. The rest of the electrodes serve as first initial open electrodes 42b. Similarly, a predetermined number of electrodes among second adjustment electrodes 52 are short-circuited as second initial short circuit electrodes 52a. The rest of the electrodes serve as second initial open electrodes 52b. As illustrated in FIG. 3, the ultrasonic vibrator 1 with the design values of the present embodiment vibrates at periods of T0 which is a design value. The horizontal axis of FIG. 3 represents time, and the vertical axis a displacement of a point A in an X direction.

Initially, the ultrasonic vibrator 1 that is longer than with the design values of the present embodiment will be described.

Figure 4:
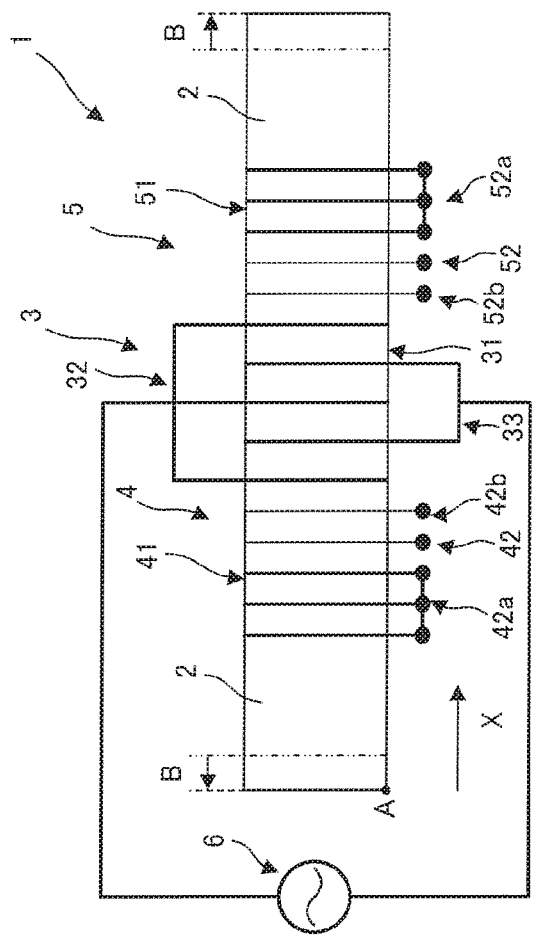
FIG. 4 illustrates a schematic diagram of the ultrasonic vibrator longer than with the design values of the present embodiment.
Figure 5:
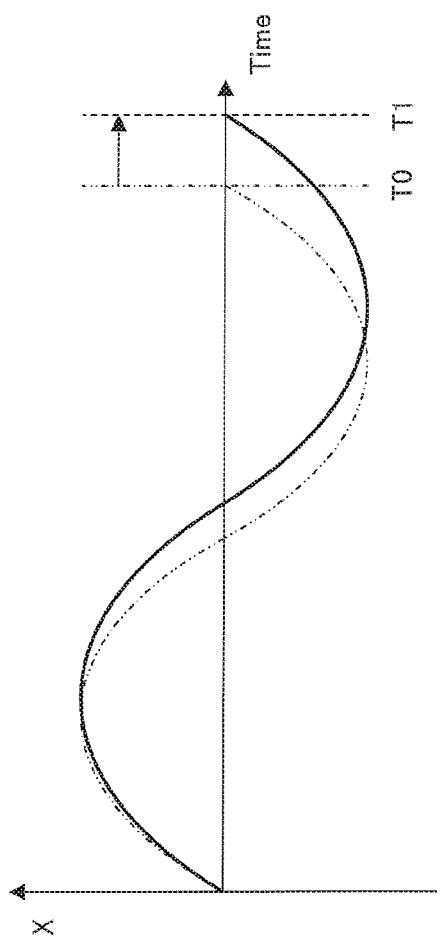
FIG. 5 illustrates one period of the ultrasonic vibrator longer than with the design values of the present embodiment.

FIG. 4 is a schematic diagram illustrating the ultrasonic vibrator 1 longer than with the design values of the present invention. FIG. 5 illustrates one period of the ultrasonic vibrator 1 longer than with the design values of the present embodiment.

As illustrated in FIG. 4, suppose that in the example where the total length is longer than with the design values of the present embodiment due to variations in the thickness dimensions of the members and the like, the ultrasonic vibrator 1 is 2B longer in the X direction. The ultrasonic vibrator 1 of such an example has a lower resonant frequency. As illustrated in FIG. 5, the ultrasonic vibrator 1 vibrates at first periods of T1 which is longer than the design period T0.

Figure 6:
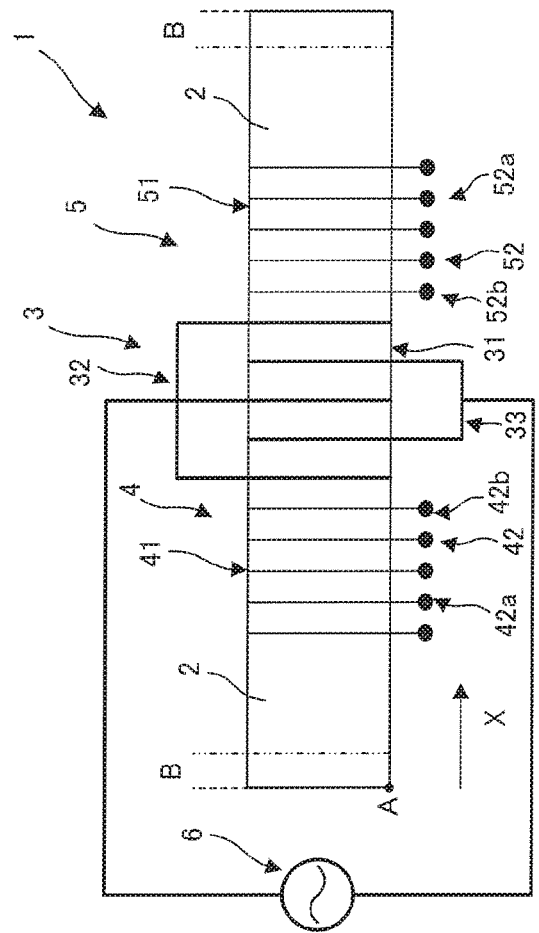
FIG. 6 illustrates a schematic diagram after control of the ultrasonic vibrator longer than with the design values of the present embodiment.
Figure 7:
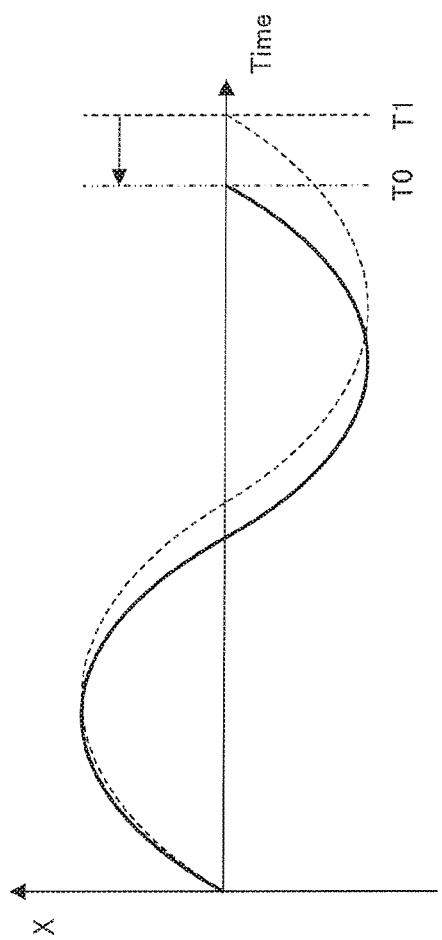
FIG. 7 illustrates one period after control of the ultrasonic vibrator longer than with the design values of the present embodiment.

FIG. 6 illustrates a schematic diagram after control of the ultrasonic vibrator 1 longer than with the design values of the present embodiment. FIG. 7 illustrates one period after control of the ultrasonic vibrator 1 longer than with the design values of the present embodiment.

As illustrated in FIG. 6, in the ultrasonic vibrator 1 of the example of being longer than with the design values of the present embodiment, the first initial short circuit electrodes 42a of the first adjustment electrodes 42 are opened and the second initial short circuit electrodes 52a of the second adjustment electrodes 52 are opened. In other words, all the first adjustment electrodes 42 and the second adjustment electrodes 52 are opened.

Opening the first initial short circuit electrodes 42a and the second initial short circuit electrodes 52a which have been short-circuited changes Young's moduli of the first adjustment piezoelectric element unit 4 and the second adjustment piezoelectric element unit 5, whereby the overall resonant frequency is adjusted. In this example, the resonant frequency of the ultrasonic vibrator 1 increases. As illustrated in FIG. 7, the ultrasonic vibrator 1 approaches the design period T0 shorter than the first period T1, or reaches the design period T0.

By opening the first initial short circuit electrodes 42a and the second initial short circuit electrodes 52a which have been short-circuited, the resonant frequency of the ultrasonic vibrator 1 in the example where the total length is longer than with the design values of the present embodiment due to variations in the thickness dimensions of the members and the like can be increased so that the ultrasonic vibrator 1 approaches the design period T0 or reaches the design period T0.

Next, the ultrasonic vibrator 1 that is shorter than with the design values of the present embodiment will be described.

Figure 8:
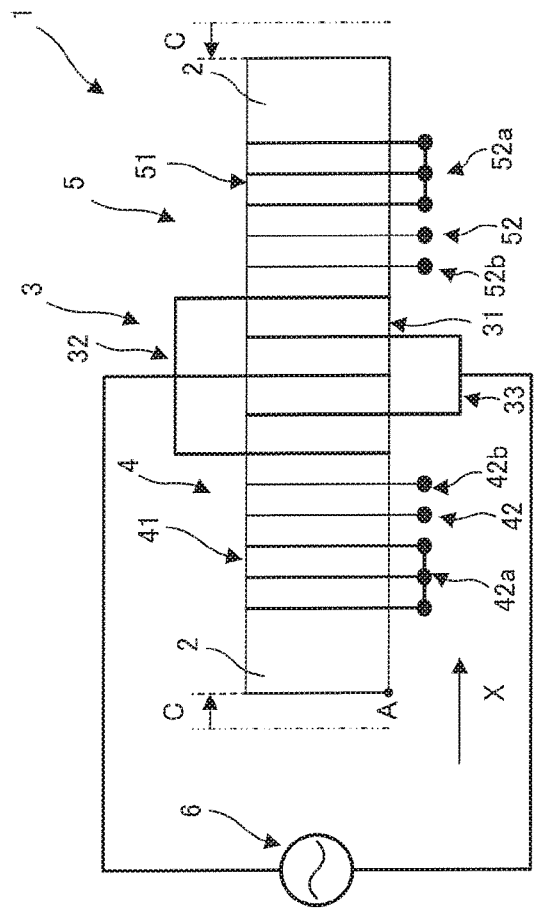
FIG. 8 illustrates a schematic diagram of the ultrasonic vibrator shorter than with the design values of the present embodiment.
Figure 9:
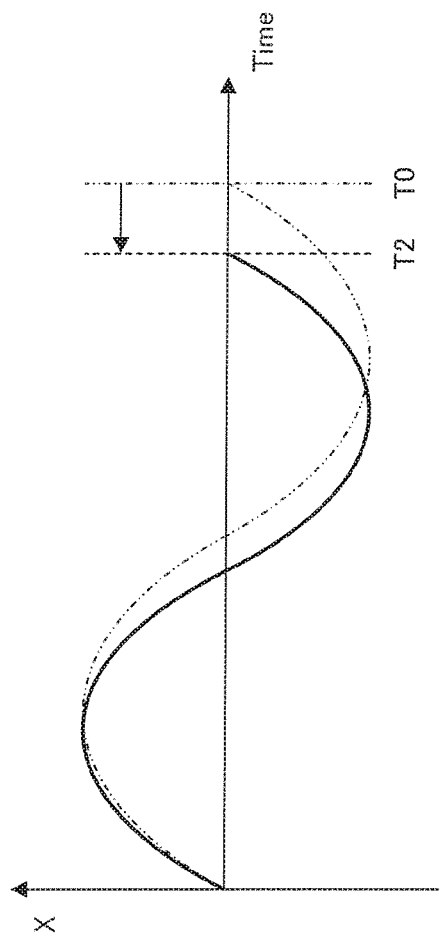
FIG. 9 illustrates one period of the ultrasonic vibrator shorter than with the design values of the present embodiment.

FIG. 8 illustrates a schematic diagram of the ultrasonic vibrator 1 shorter than with the design values of the present embodiment. FIG. 9 illustrates one period of the ultrasonic vibrator 1 shorter than with the design values of the present embodiment.

As illustrated in FIG. 8, suppose that in the example where the total length is shorter than with the design values of the present embodiment due to variations in the thickness dimensions of the members and the like, the ultrasonic vibrator 1 is 2C shorter in the X direction. The ultrasonic vibrator 1 of such an example has a lower resonant frequency. As illustrated in FIG. 9, the ultrasonic vibrator 1 vibrates at second periods of T2 which is shorter than the design period T0.

Figure 10:
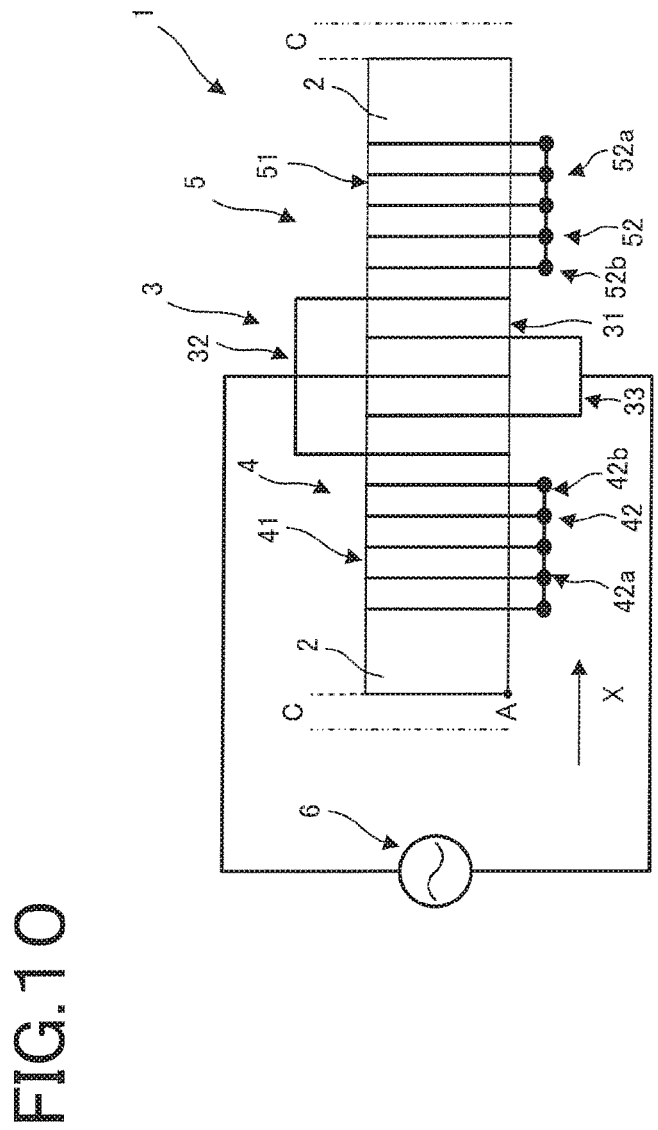
FIG. 10 illustrates a schematic diagram after control of the ultrasonic vibrator shorter than with the design values of the present embodiment.
Figure 11:
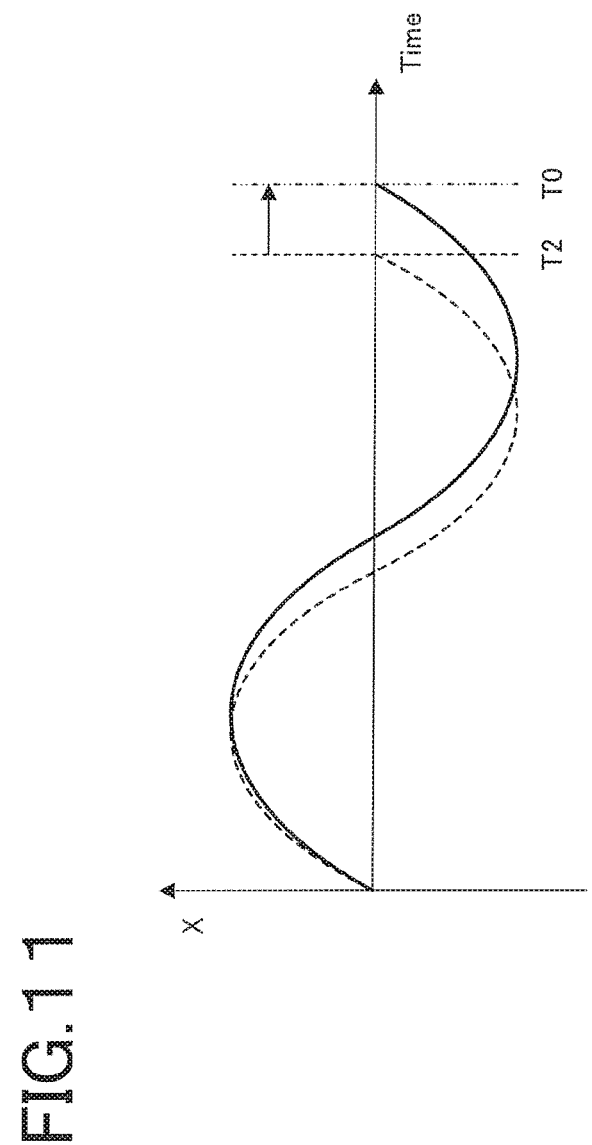
FIG. 11 illustrates one period after control of the ultrasonic vibrator shorter than with the design values of the present embodiment.

FIG. 10 illustrates a schematic diagram after control of the ultrasonic vibrator 1 shorter than with the design values of the present embodiment. FIG. 11 illustrates one period after control of the ultrasonic vibrator 1 shorter than with the design values of the present embodiment.

As illustrated in FIG. 10, in the ultrasonic vibrator 1 of the example of being shorter than with the design values of the present embodiment, the first initial open electrodes 42b of the first adjustment electrodes 42 are short-circuited and the second initial open electrodes 52b of the second adjustment electrodes 52 are short-circuited. In other words, all the first adjustment electrodes 42 are short-circuited, and all the second adjustment electrodes 52 are short-circuited.

Short-circuiting the first initial open electrodes 42b and the second initial open electrodes 52b which have been open changes Young's moduli of the first adjustment piezoelectric element unit 4 and the second adjustment piezoelectric element unit 5, whereby the overall resonant frequency is adjusted. In this example, the resonant frequency of the ultrasonic vibrator 1 decreases. As illustrated in FIG. 11, the ultrasonic vibrator 1 approaches the design period T0 longer than the second period T2, or reaches the design period T0.

As described above, by short-circuiting the first initial open electrodes 42b and the second initial open electrodes 52b which have been open, the resonant frequency of the ultrasonic vibrator 1 in the example where the total length is shorter than with the design values of present embodiment due to variations in the thickness dimensions of the members and the like can be reduced so that the ultrasonic vibrator 1 approaches the design period T0 or reaches the design period T0.

Next, differences in performance depending on the materials of the piezoelectric elements will be described.

Figure 12:
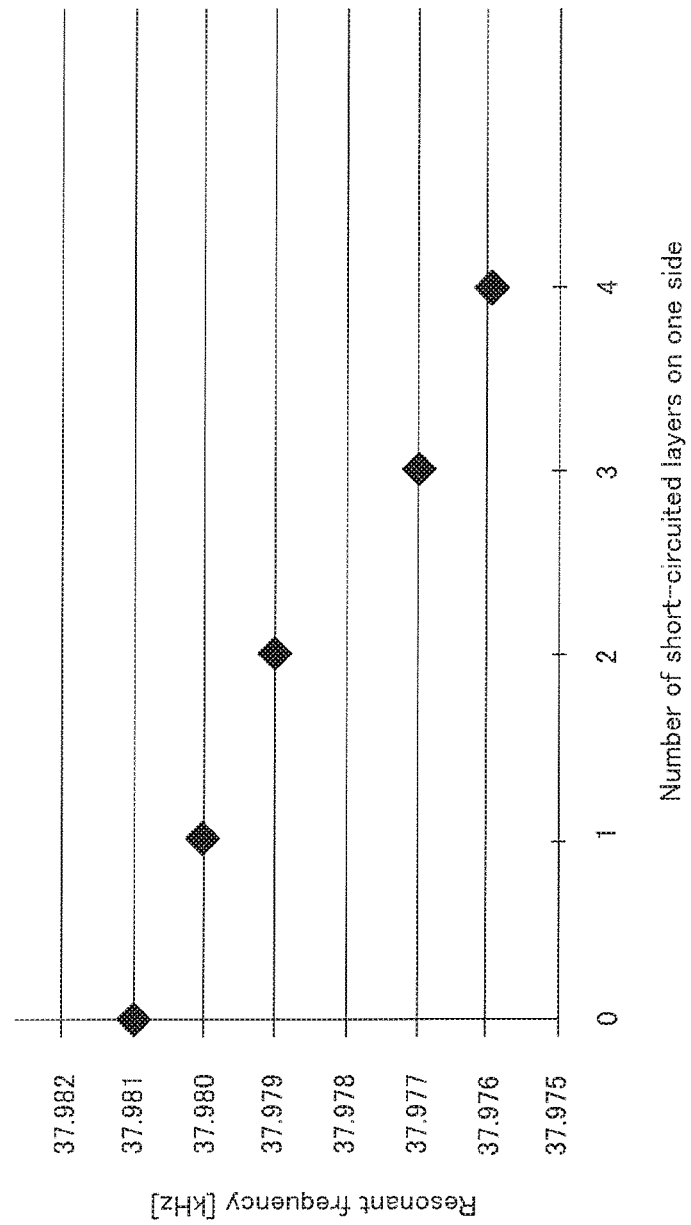
FIG. 12 illustrates a relationship between the number of short-circuited layers and a resonant frequency when adjustment piezoelectric elements are made of lead zirconate titanate.
Figure 13:
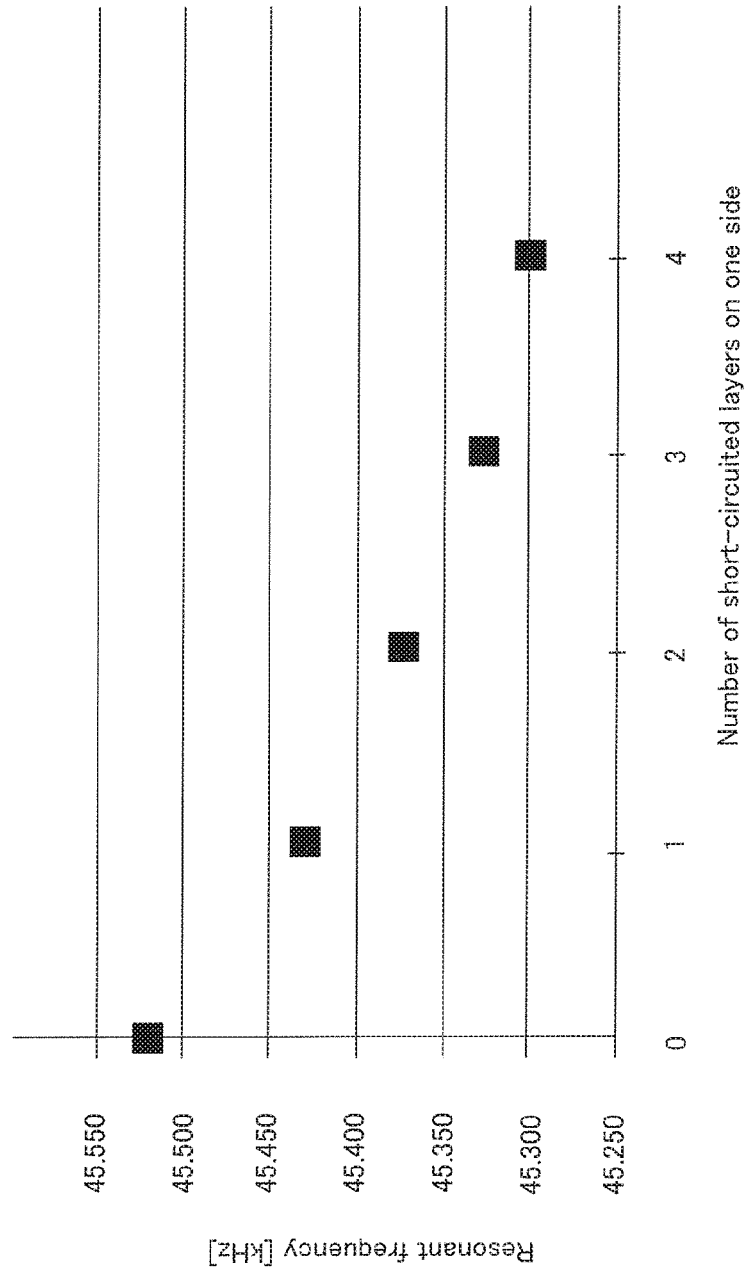
FIG. 13 illustrates a relationship between the number of short-circuited layers and the resonant frequency when the adjustment piezoelectric elements are made of lithium niobate.
Figure 14:
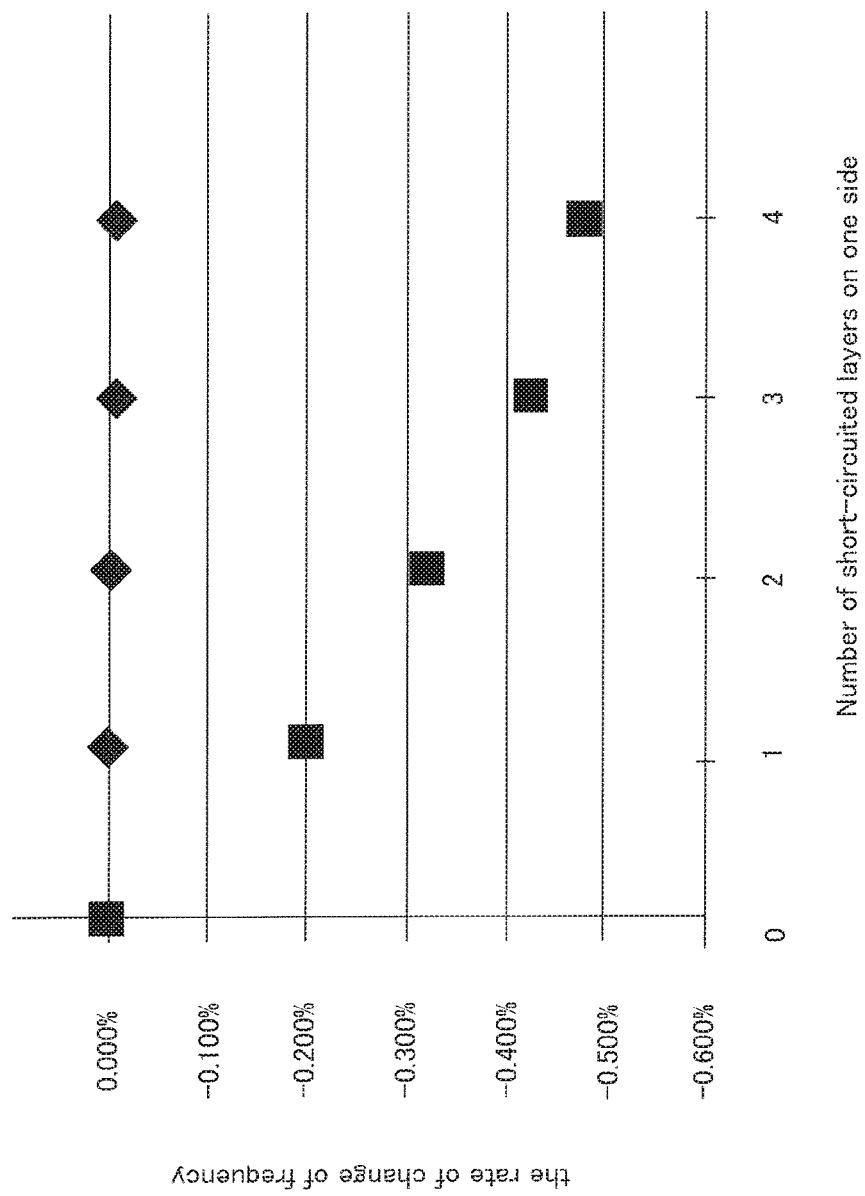
FIG. 14 illustrates a relationship between the number of short-circuited layers and the rate of change of frequency when the adjustment piezoelectric elements are made of lead zirconate titanate and when the adjustment piezoelectric elements are made of lithium niobate.

FIG. 12 illustrates a relationship between the number of short-circuited layers and the resonant frequency when the adjustment piezoelectric elements 41 and 51 are made of lead zirconate titanate. FIG. 13 illustrates a relationship between the number of short-circuited layers and the resonant frequency when the adjustment piezoelectric elements are made of lithium niobate. FIG. 14 illustrates a relationship between the number of short-circuited layers and the rate of change of frequency when the adjustment piezoelectric elements are made of lead zirconate titanate and when the adjustment piezoelectric elements are made of lithium niobate.

As illustrated in FIGS. 12 and 13, the resonant frequency decreases with the increasing number of short-circuited layers regardless of which material is used. However, as illustrated in FIG. 14, the use of lithium niobate provides a higher rate of decrease than the use of lead zirconate titanate does. Considering the adjustment widths of the adjustment piezoelectric elements 41 and 51 in the design phase, lithium niobate is preferably used if the adjustment widths are large. Lead zirconate titanate is preferably used if the adjustment widths are small. The adjustment piezoelectric elements 41 and 51 made of lithium niobate and the adjustment piezoelectric elements 41 and 51 made of lead zirconate titanate both may be stacked and used depending on the situation.

Next, an ultrasonic vibrator 1 according to another embodiment will be described.

As illustrated in FIG. 6, the ultrasonic vibrator 1 may have design values such that the first adjustment electrodes 42 and the second adjustment electrodes 52 are all open, and the adjustment electrodes may be short-circuited for adjustment. As illustrated in FIG. 10, the ultrasonic vibrator 1 may have design values such that the first adjustment electrodes 42 and the second adjustment electrodes 52 are all short-circuited, and the adjustment electrodes may be opened for adjustment. That is, the design values of the adjustment piezoelectric elements 41 and 51, short-circuited or open, may be determined according to the performance desired by the designer or user.

At least either one of the first adjustment piezoelectric element unit 4 and the second adjustment piezoelectric element unit 5 may be used. The numbers of stacked layers of the first adjustment piezoelectric elements 41 and the second adjustment piezoelectric elements 51 may be determined according to the performance desired by the designer or user.

Figure 15:
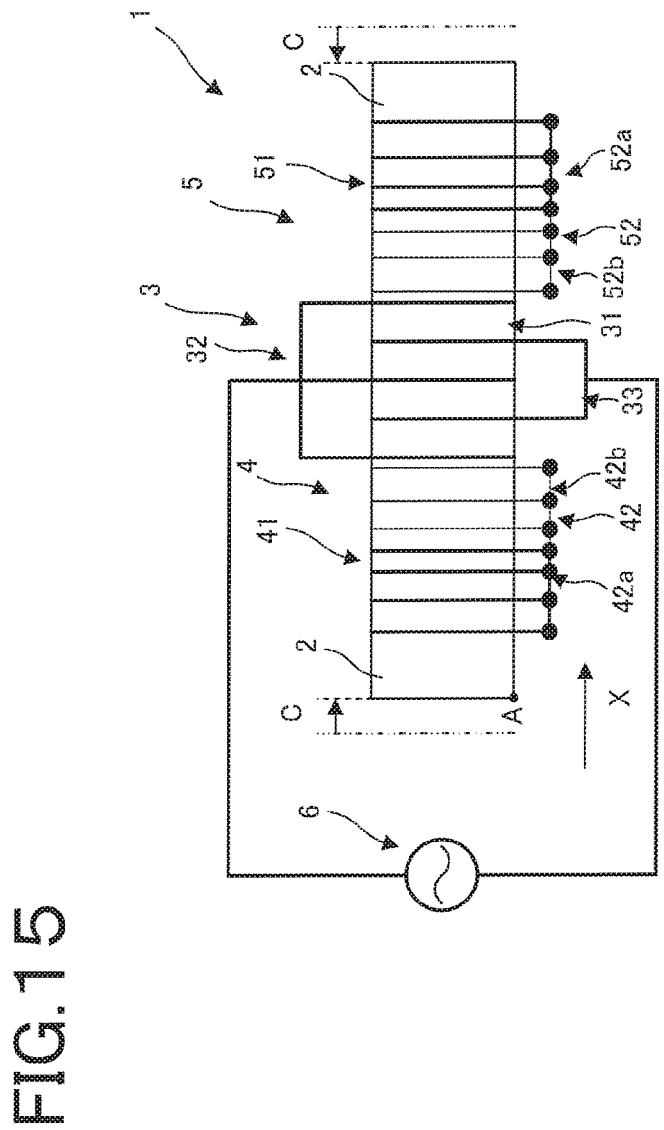
FIG. 15 illustrates a case in which a first adjustment piezoelectric element unit and a second adjustment piezoelectric element unit are formed to include first adjustment piezoelectric elements and second adjustment piezoelectric elements having respective different thicknesses.

FIG. 15 illustrates a case in which the first adjustment piezoelectric element unit 4 and the second adjustment piezoelectric element unit 5 are formed to include first adjustment piezoelectric elements 41 and second adjustment piezoelectric elements 51 of respective different thicknesses.

As illustrated in FIG. 15, the first adjustment piezoelectric element unit 4 and the second adjustment piezoelectric element unit 5 may include the first adjustment piezoelectric elements 41 and the second adjustment piezoelectric elements 51 of different thicknesses, respectively. The formation with different thicknesses can modify the variation width of the frequency between a short-circuited state and an open state, whereby fine adjustments can be made for the resonant frequency.

Figure 16:
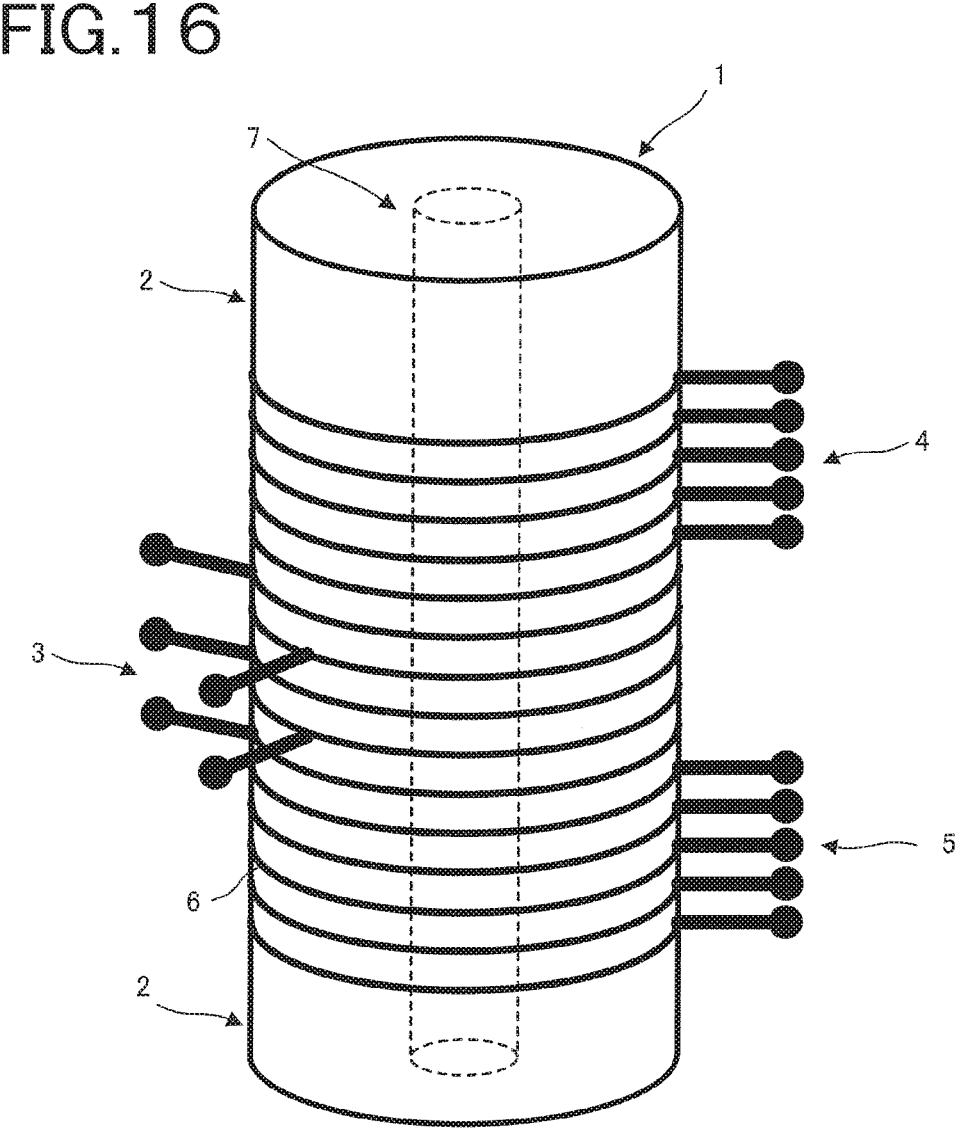
FIG. 16 illustrates an ultrasonic vibrator according to another embodiment.

FIG. 16 illustrates an ultrasonic vibrator 1 according to another embodiment.

The first adjustment piezoelectric element unit 4 and the second adjustment piezoelectric element unit 5 according to the present embodiment may be applied to ultrasonic vibrators 1 of other aspects. For example, as illustrated in FIG. 16, the first adjustment piezoelectric element unit 4 and the second adjustment piezoelectric element unit 5 can be applied to a Langevin vibrator 1 tightened with a bolt 7, and the like. The ultrasonic vibrator 1 may have an axial cross section of circular, square, oblong rectangular, or other rectangular shape.

Figure 17:
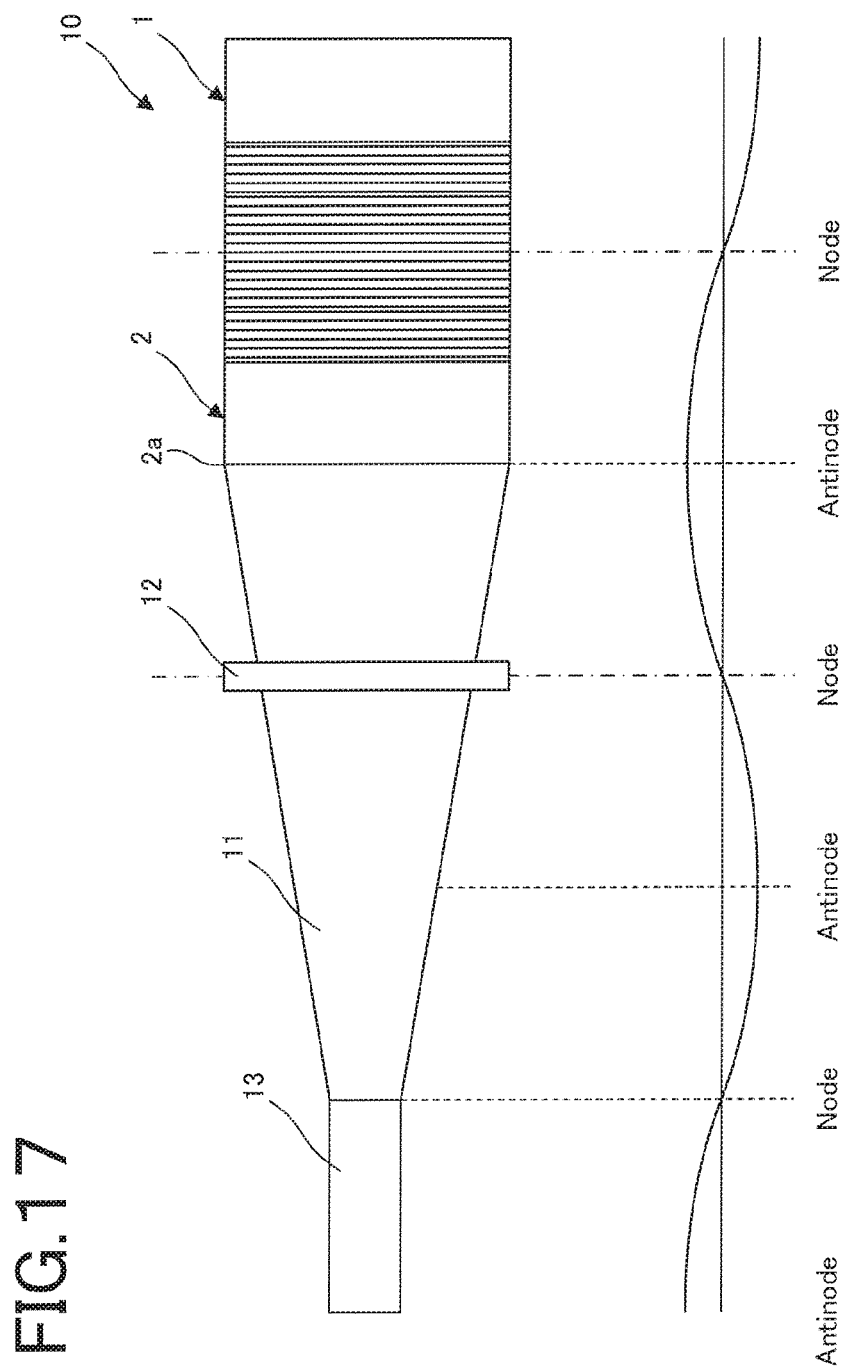
FIG. 17 illustrates a part of a treatment device to which the ultrasonic vibrator according to the present embodiment is applied.

FIG. 17 illustrates a part of a treatment device 10 to which the ultrasonic vibrator 1 according to the present embodiment is applied. FIG. 17A is a diagram illustrating the treatment device. FIG. 17B is a diagram illustrating how the treatment device vibrates.

As illustrated in FIG. 17, the treatment device 10 according to the present embodiment includes a horn portion 11 which is attached to one of the metal blocks 2 of the ultrasonic vibrator 1, a flange portion 12 which is formed on the horn portion 11, and an end portion 13 which is attached to the end of the horn portion 11.

The treatment device 10 transmits vibrations of the ultrasonic vibrator 1 to vibrate and form nodes and antinodes. For example, at the time of design, as illustrated in FIG. 17, the center of the ultrasonic vibrator 1 is preferably set to be a node, an end 2a of the metal block 2 an antinode, the flange portion 12 a node, and the topmost end of the end portion 13 as an antinode.

However, actually completed products may have vibration nodes and antinodes in different positions due to variations in the thickness dimensions of the members, etc. Then, the ultrasonic vibrator 1 according to the present embodiment can be used to adjust the deviations of the vibration nodes and antinodes. The horn portion 11, the flange portion 12, and the end portion 13 may be changed in length as long as the positions of the vibration nodes and antinodes, i.e., the periods match.

Figure 18:
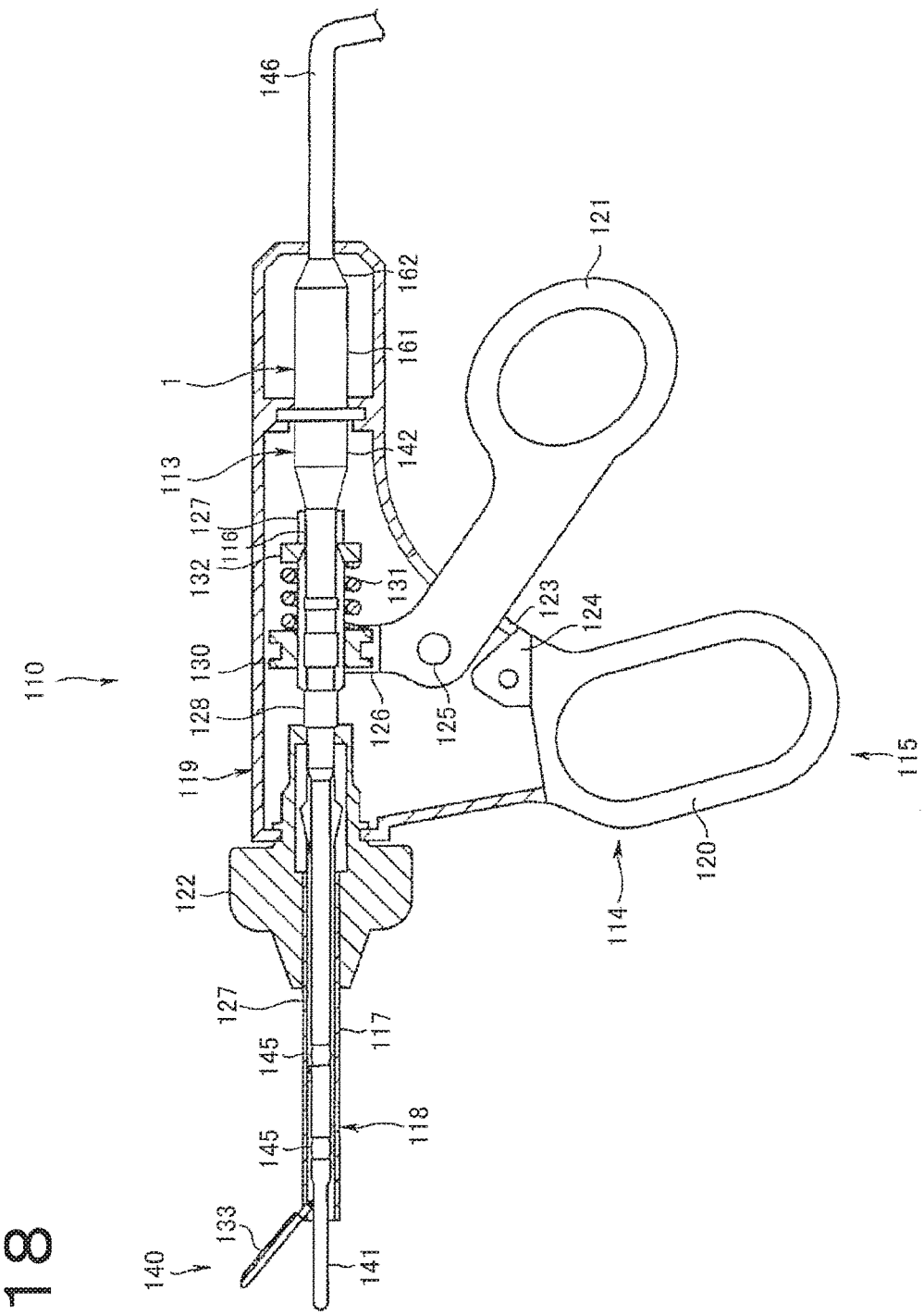
FIG. 18 illustrates an overall configuration of an ultrasonic medical device according to the present embodiment.
Figure 19:
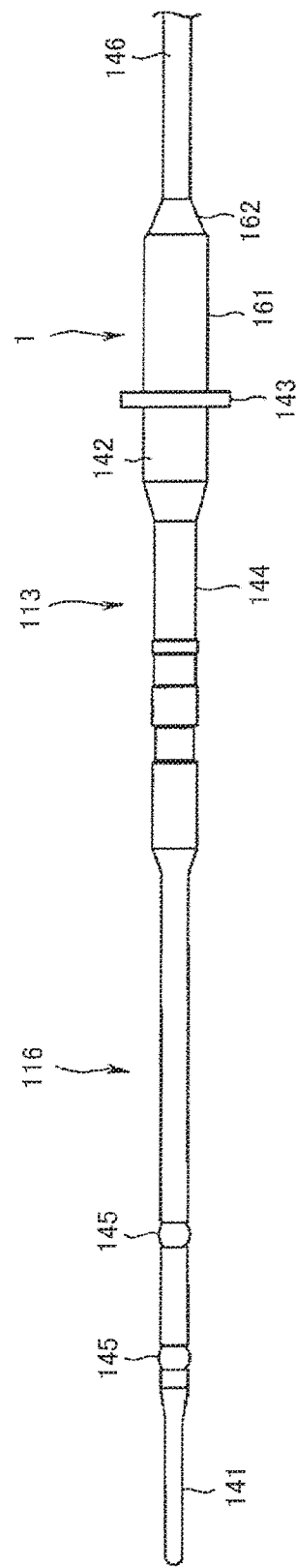
FIG. 19 illustrates a schematic configuration of an entire vibrator unit of the ultrasonic medical device according to the present embodiment.

FIG. 18 illustrates an overall configuration of an ultrasonic medical device according to the present embodiment. FIG. 19 illustrates a schematic configuration of an entire vibrator unit of the ultrasonic medical device according to the present embodiment.

An ultrasonic medical device 110 illustrated in FIG. 18 includes a vibrator unit 113 which includes an ultrasonic vibrator 1 for mainly generating ultrasonic vibrations, and a handle unit 114 which is intended to administer treatment to an affected part by using the ultrasonic vibrations.

The handle unit 114 includes an operation portion 115, an insertion sheath portion 118 including a long mantle tube 117, and an end treatment portion 140. A bottom end of the insertion sheath portion 118 is axially rotatably attached to the operation portion 115. The end treatment portion 140 is arranged at the end of the insertion sheath portion 118. The operation portion 115 of the handle unit 114 includes an operation portion main body 119, a fixed handle 120, a movable handle 121, and a rotary knob 122. The operation portion main body 119 is integrally formed with the fixed handle 120.

A slit 123 for the movable handle 121 to be inserted through is formed in a back side of the connecting portion between the operation portion main body 119 and the fixed handle 120. An upper part of the movable handle 121 is passed through the slit 123 and extended into the operation portion main body 119. A handle stopper 124 is fixed to a lower end of the slit 123. The movable handle 121 is rotatably attached to the operation portion main body 119 via a handle spindle 125. As the movable handle 121 is operated to rotate about the handle spindle 125, the movable handle 121 is opened and closed with respect to the fixed handle 120.

A coupling arm 126 of generally U shape is arranged on the top end of the movable handle 121. The insertion sheath portion 118 includes the mantle tube 117 and an operation pipe 127 which is axially movably inserted through the mantle tube 117. A large diameter portion 128 having a diameter larger than that on the top end side is formed on the bottom end of the mantle tube 117. The rotary nob 122 is mounted on the periphery of the large diameter portion 128.

A ring-shaped slider 130 is axially movably arranged on the outer peripheral surface of the operation pipe 127. A fixed ring 132 is arranged behind the slider 130 via a coil spring (elastic member) 131.

A bottom end of a gripping part 133 is rotatably coupled to the top end of the operation pipe 127 via an application pin. The gripping part 133 constitutes a treatment portion of the ultrasonic medical device 110 with an end portion 141 of a probe 116. During operation in which the operation pipe 127 moves axially, the gripping part 133 is pushed forward or pulled back via the application pin. During operation in which the operation pipe 127 is operated to move to the near side, the gripping part 133 is rotated counterclockwise about a fulcrum pin via the application pin. The gripping part 133 is thereby rotated in a direction of approaching the end portion 141 of the probe 116 (closing direction). Here, the gripping part 133 of swing type and the end portion 141 of the probe 116 can grip living body tissue therebetween.

With the living body tissue gripped thus, electric power is supplied from an ultrasonic power supply to the ultrasonic vibrator 1 to vibrate the ultrasonic vibrator 1. The ultrasonic vibrations are transmitted to the the end portion 141 of the probe 116. The ultrasonic vibrations are then used to administer treatment to the living body tissue gripped between the gripping part 133 and the end portion 141 of the probe 116.

As illustrated in FIG. 19, the vibrator unit 113 is formed by integrally assembling the ultrasonic vibrator 1 and the probe 116 which is a bar-shaped vibration transmission member for transmitting the ultrasonic vibrations generated by the ultrasonic vibrator 1.

A horn 142 for amplifying the amplitude of the ultrasonic vibrator is connected to the ultrasonic vibrator 1. The horn 142 is made of duralumin, stainless steel, or a titanium alloy such as 64Ti (Ti-6Al-4V). The horn 142 is formed in a conical shape of decreasing in the outer diameter toward the top end side. An outward flange 143 is formed on the outer periphery of the bottom end. Note that the shape of the horn 142 is not limited to the conical shape.

An exponential shape of exponentially decreasing in the outer diameter toward the top end side, a stepped shape of decreasing in the outer diameter stepwise toward the top end side, and other shapes may be used.

The probe 116 includes a probe main body 144 which is made of a titanium alloy such as 64Ti (Ti-6Al-4V). The ultrasonic vibrator 1 connected to the foregoing horn 142 is arranged on the bottom end side of the probe main body 144. In such a manner, the vibrator unit 113 is formed to integrate the probe 116 and the ultrasonic vibrator 1. The probe main body 144 of the probe 116 and the horn 142 are threaded attached, whereby the probe main body 144 and the horn 142 are joined to each other.

The ultrasonic vibrations generated by the ultrasonic vibrator 1 are amplified by the horn 142 before transmitted to the end portion 141 side of the probe 116. The treatment portion to be described later for treating living body tissue is formed on the end portion 141 of the probe 116.

Two rubber linings 145 made of ring-shaped elastic members are attached to the outer peripheral surface of the probe main body 144 in several axial antinode positions of vibrations at a distance therebetween. These rubber linings 145 prevent a contact between the outer peripheral surface of the probe main body 144 and the operation pipe 127 to be described later. More specifically, when the insertion sheath portion 118 is assembled, the probe 116 serving as a vibrator-integrated probe is inserted into the operation pipe 127. Here, the rubber linings 145 prevent a contact between the outer peripheral surface of the probe main body 144 and the operation pipe 127.

The ultrasonic vibrator 1 is electrically connected to a not-illustrated power supply apparatus main body that supplies a current for generating ultrasonic vibrations, via an electrical cable 146. Electrical power is supplied from the power supply apparatus main body to the ultrasonic vibrator 1 through the wiring inside the electrical cable 146, whereby the ultrasonic vibrator 1 is driven. The vibrator unit 113 includes the ultrasonic vibrator 1 which generates ultrasonic vibrations, the horn 142 which amplifies the generated ultrasonic vibrations, and the probe 116 which transmits the amplified ultrasonic vibrations.

Figure 20:
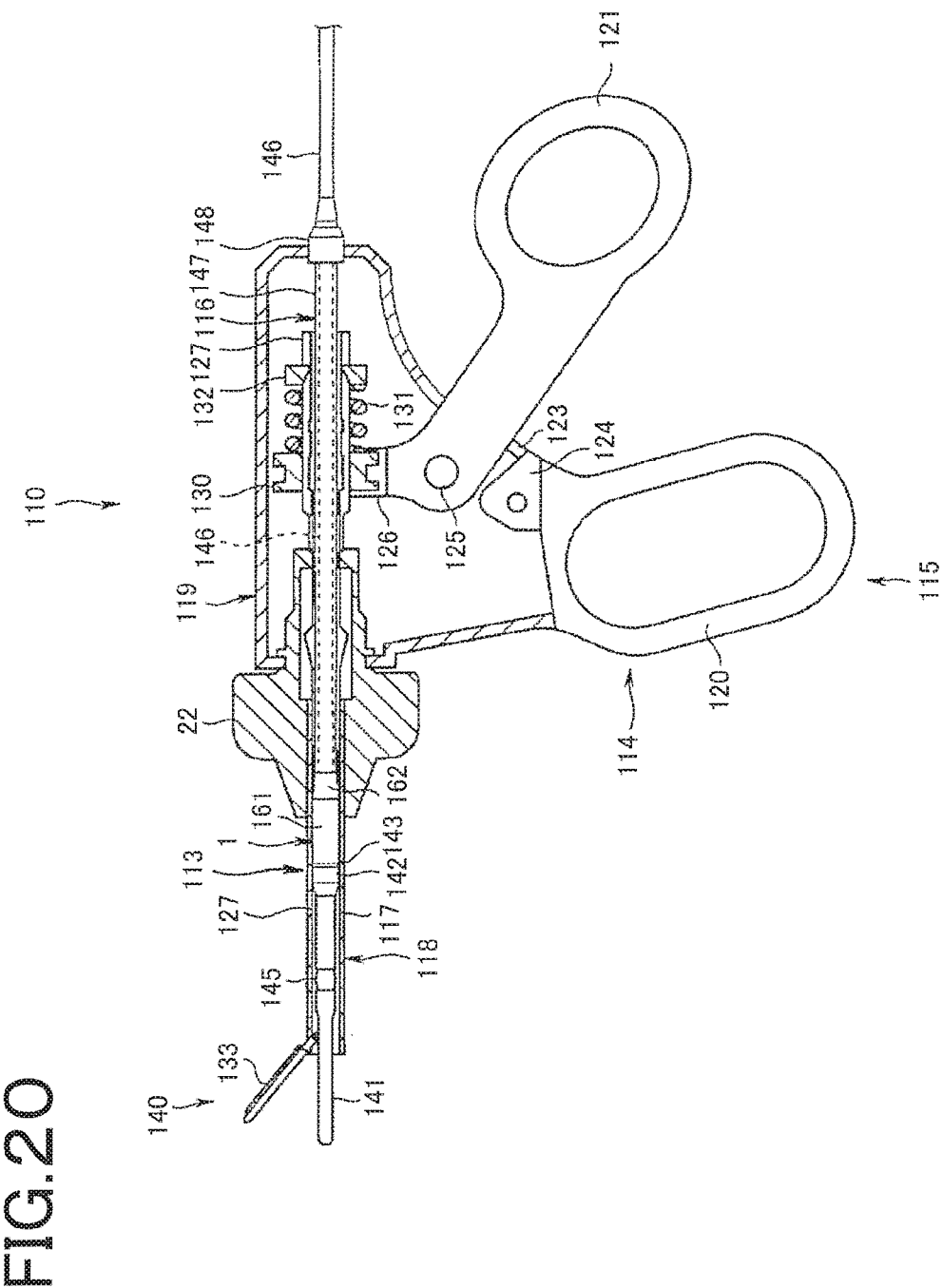
FIG. 20 illustrates an overall configuration of an ultrasonic medical device according to another aspect of the ultrasonic medical device of the present embodiment.

FIG. 20 illustrates an overall configuration of an ultrasonic medical device according to another aspect of the ultrasonic medical device of the present embodiment.

The ultrasonic vibrator 1 and the vibrator unit 113 do not necessarily need to be accommodated in the operation portion main body 119 as illustrated in FIG. 18, and may be accommodated in the operation pipe 127 as illustrated in FIG. 20. In the ultrasonic medical device 110 of FIG. 20, the electrical cable 146 lying between a bending stopper 162 of the ultrasonic vibrator 1 and a connector 148 arranged on the bottom portion of the operation portion main body 119 is inserted through and accommodated in a metal pipe 147. The connector 148 is not an indispensable component, and the electrical cable 146 may be extended into the operation portion main body 119 and directly connected to the bending stopper 162 of the ultrasonic vibrator 1. With the configuration illustrated in FIG. 20, the ultrasonic medical device 110 can further save space inside the operation portion main body 119. The function of the ultrasonic medical device 110 of FIG. 20 is the same as that of FIG. 18. A detailed description thereof will thus be omitted.

As described above, the ultrasonic vibrator 1 according to the present embodiment includes the two metal blocks 2, the driving piezoelectric element unit 3 which is arranged between the metal blocks 2 and produces a piezoelectric effect to vibrate by application of an alternating voltage, and at least one adjustment piezoelectric element unit 4 or 5 which is arranged between a metal block 2 and the driving piezoelectric element unit 3 in an insulated state and changes Young's modulus. The ultrasonic vibrator 1 can thus adjust the resonant frequency while maintaining the driving force.

In the ultrasonic vibrator 1 according to the present embodiment, the adjustment piezoelectric element units 4 and 5 include the first adjustment piezoelectric element unit 4 which is arranged between one of the metal blocks 2 and the driving piezoelectric element unit 3, and the second adjustment piezoelectric element unit 5 which is arranged between the other metal block 2 and the driving piezoelectric element unit 3. The resonant frequency can thus be precisely adjusted.

In the ultrasonic vibrator 1 according to the present embodiment, the adjustment piezoelectric element units 4 and 5 are symmetrically arranged with respect to the driving piezoelectric element unit 3. The resonant frequency can thus be adjusted more precisely.

In the ultrasonic vibrator 1 according to the present embodiment, the driving piezoelectric element unit 3 includes the plurality of stacked driving piezoelectric elements 31 and the driving electrodes 32 and 33 which are joined to the respective driving piezoelectric elements 31 and connected to the alternating-current power supply for applying the alternating voltage. The adjustment piezoelectric element units 4 include the plurality of stacked adjustment piezoelectric elements 41 and 51 and the adjustment electrodes 42 and 52 which are joined to the respective adjustment piezoelectric elements 41 and 51. The resonant frequency can thus be adjusted with higher precision.

In the ultrasonic vibrator 1 according to the present embodiment, at least some of the adjustment electrodes 42 and 52 are short-circuited in advance. Young's moduli of the adjustment piezoelectric element units 4 and 5 are changed by opening the short-circuited ones of the adjustment electrodes 42 and 52 or short-circuiting electrodes other than the short-circuited ones of the adjustment electrodes 42 and 52. The resonant frequency can thus be adjusted in a well-balanced manner.

In the ultrasonic vibrator 1 according to the present embodiment, all the adjustment electrodes 42 and 52 are short-circuited. Young's moduli of the adjustment piezoelectric element units 4 and 5 are changed by opening some of the short-circuited electrodes 42 and 52. The resonant frequency can thus be increased with high precision.

In the ultrasonic vibrator 1 according to the present embodiment, all the adjustment electrodes 42 and 52 are open. Young's moduli of the adjustment piezoelectric element units 4 and 5 are changed by short-circuiting some of the open adjustment electrodes 42 and 52. The resonant frequency can thus be reduced with high precision.

In the ultrasonic vibrator 1 according to the present embodiment, at least some of the plurality of stacked adjustment piezoelectric elements 41 and 51 have different thicknesses. The resonant frequency can thus be adjusted with higher precision.

In the ultrasonic vibrator 1 according to the present embodiment, the metal blocks 2 are made of a 64 titanium alloy (64Ti), and the driving piezoelectric elements 31 and the adjustment piezoelectric elements 41 and 51 are made of lithium niobate ($LiNbO_3$). The adjustment width of the resonant frequency can thus be increased.

The ultrasonic treatment device 10 according to the present embodiment includes the foregoing ultrasonic vibrator 1 and the end portion 13 to which ultrasonic vibrations generated by the ultrasonic vibrator 1 are transmitted and which treats living body tissue. The ultrasonic treatment device 10 can thus adjust the resonant frequency while maintaining the driving force.

The present invention is not limited by the embodiments. That is, while the description of the embodiments includes a lot of specific details for illustrative purpose, it will be understood by those skilled in the art that various variations and modifications may be made to such details without departing from the scope of the present invention. The exemplary embodiments of the present invention have thus been described without impairing the generality of or limiting the claimed inventions.

REFERENCE SIGNS LIST

1: Ultrasonic vibrator
2: Metal block
3: Driving piezoelectric element unit (driving unit)
31: Driving piezoelectric element
32: First driving electrode
33: Second driving electrode
4: First adjustment piezoelectric element unit (adjustment unit, first adjustment unit)
41: First adjustment piezoelectric element (adjustment piezoelectric element)
42: First adjustment electrode (adjustment electrode)
5: Second adjustment piezoelectric element unit (adjustment unit, second adjustment unit)
51: Second adjustment piezoelectric element (adjustment piezoelectric element)
52: Second adjustment electrode (adjustment electrode)
6: Bonding material

The invention claimed is:
1. An ultrasonic vibrator comprising:
two metal blocks;
a driving unit arranged between the two metal blocks, the driving unit being configured to produce a piezoelectric effect to vibrate by application of an alternating voltage; and at least one adjustment unit arranged between the two metal blocks and the driving unit in an insulated state, the adjustment unit being configured to change Young's modulus, wherein:

the at least one adjustment unit comprises a plurality of stacked adjustment piezoelectric elements and adjustment electrodes that are joined to the respective adjustment piezoelectric elements, and Young's modulus of the adjustment unit is changed by opening or short-circuiting at least one of the adjustment electrodes.

2. The ultrasonic vibrator according to claim 1, wherein the adjustment unit comprises:
a first adjustment unit arranged between one of the two metal blocks and the driving unit, and
a second adjustment unit arranged between the other of the two metal blocks and the driving unit.

3. The ultrasonic vibrator according to claim 1, wherein the adjustment unit is symmetrically arranged with respect to the driving unit.

4. The ultrasonic vibrator according to claim 1, wherein:
at least some of the adjustment electrodes are short-circuited; and
Young's modulus of the adjustment unit is changed by opening the short-circuited ones of the adjustment electrodes or short-circuiting electrodes other than the short-circuited ones of the adjustment electrodes.

5. The ultrasonic vibrator according to claim 1, wherein:
all the adjustment electrodes are short-circuited; and
Young's modulus of the adjustment unit is changed by opening some of the short-circuited adjustment electrodes.

6. The ultrasonic vibrator according to claim 1, wherein:
all the adjustment electrodes are open; and
Young's modulus of the adjustment unit is changed by short-circuiting some of the open adjustment electrodes.

7. The ultrasonic vibrator according to claim 1, wherein at least one of the plurality of stacked adjustment piezoelectric elements has a thickness different from a thickness of other ones of the plurality of stacked adjustment piezoelectric elements.

8. The ultrasonic vibrator according to claim 1, wherein:
the two metal blocks are made of a 64 titanium alloy (64Ti); and
the driving piezoelectric elements and the adjustment piezoelectric elements are made of lithium niobate (LiNbO3).

9. An ultrasonic treatment device comprising:
the ultrasonic vibrator according to claim 1; and
an end portion to which ultrasonic vibrations generated by the ultrasonic vibrator are transmitted and which treats living body tissue.

* * * * *